United States Patent
Barnes et al.

(10) Patent No.: US 6,881,722 B2
(45) Date of Patent: Apr. 19, 2005

(54) SARATIN FOR INHIBITING PLATELET ADHESION TO COLLAGEN

(75) Inventors: Christopher Barnes, Bad Soden (DE); Matthias Frech, Darmstadt (DE); Uwe Hofmann, Balkhausen (DE); Johannes Gleitz, Darmstadt (DE); Wolfgang Strittmatter, Ober-Ramstadt (DE)

(73) Assignee: Merck GmbH, Darmstadt (DE)

( * ) Notice: Subject to any disclaimer, the term of this patent is extended or adjusted under 35 U.S.C. 154(b) by 0 days.

(21) Appl. No.: 10/362,476

(22) PCT Filed: Aug. 23, 2001

(86) PCT No.: PCT/EP01/09746

§ 371 (c)(1),
(2), (4) Date: Feb. 24, 2003

(87) PCT Pub. No.: WO02/15919

PCT Pub. Date: Feb. 28, 2002

(65) Prior Publication Data

US 2003/0190342 A1 Oct. 9, 2003

(30) Foreign Application Priority Data

Aug. 25, 2000 (EP) .......................................... 00118542

(51) Int. Cl.[7] ............................................. A61K 38/17
(52) U.S. Cl. ..................... 514/12; 530/350; 424/94.64
(58) Field of Search ........................... 514/12; 530/350; 424/94.64

(56) References Cited

U.S. PATENT DOCUMENTS

| | | | | |
|---|---|---|---|---|
| 4,898,734 A | * | 2/1990 | Mathiowitz et al. | ........ 424/426 |
| 5,246,715 A | | 9/1993 | Eldor et al. | |
| 5,616,608 A | * | 4/1997 | Kinsella et al. | ............. 514/449 |

FOREIGN PATENT DOCUMENTS

| WO | WO 9207005 | 4/1992 |
|---|---|---|
| WO | WO 9501375 | 1/1995 |
| WO | WO 0056885 | 9/2000 |

OTHER PUBLICATIONS

Barnes CS et al., "Production and characterization of saratin, an inhibitor of von Willebrand factor–dependent platelet adhesion to collagen," Seminars in Thrombosis and Hemostasis, vol. 27, No. 4, pp. 337–348, Aug. 2001.

* cited by examiner

*Primary Examiner*—Jon Weber
*Assistant Examiner*—Anand Desai
(74) *Attorney, Agent, or Firm*—Millen, White, Zelano, Branigan, P.C.

(57) ABSTRACT

Use of the polypeptide Saratin for the manufacture of a medicament having the capability to significantly decrease platelet adhesion and platelet accumulation after vascular injuries or endarterectomy. The invention furthermore relates to a novel medical use of Saratin as an inhibitor of thrombosis and intimal hyperplasia, wherein the Saratin polypeptide may be used locally as a topical agent or as a coating on, or otherwise incorporated or associated with medical devices.

21 Claims, 9 Drawing Sheets

SARATIN FOR INHIBITING PLATELET ADHESION TO COLLAGEN

SUMMARY OF THE INVENTION

The invention relates to the effect of a polypeptide called Saratin that significantly decreases platelet adhesion and accumulation after vascular injuries such as endarterectomy. The invention furthermore relates to the inhibition of vWF-dependent binding of platelets to vascular wall collagens under conditions of elevated shear and in more detail, to a novel medical use of Saratin as an inhibitor of thrombosis wherein said polypeptide may be used locally as a topical agent or as a coating for medical devices.

FIELD OF THE INVENTION

The adhesion of blood cells especially platelets to the wall of injured blood vessels is a well known phenomen in angioplasty and surgical procedures. Such injuries may occure during various surgical and percutaneous therapies that have been developed to reopen blocked channels, conduits, and other lumens, to remove diseased tissue, and to implant substitute tissue, or components thereof.

Various types of intervention techniques have been developed which facilitate the reduction or removal of the blockage in the blood vessel, allowing increased blood flow through the vessel. One technique for treating stenosis or occlusion of a blood vessel is percutaneous balloon angioplasty. A balloon catheter is threaded through the patient's arterial system and inserted into the narrowed or blocked area, and the balloon is inflated to expand the constricted area. Percutaneous transluminal angioplasty (PTCA) is the most widely angioplasty method used to open obstructed atherosclerotic arteries.

Generally, angioplasty procedures produce excellent results obviating the need for bypass surgery, but in about 30–40% of patients, an ostensibly successful initial dilatation of the artery may be followed by a renarrowing of the vessel (restenosis) some 3 to 9 months later. If this restenosis is severe, the patients may require a second angioplasty procedure, often with implantation of a stent to act as a scaffold in the vessel.

In other cases arterial reconstruction under by-pass surgery, which is a higher risk procedure, may be required. With more than 800,000 PTCA procedures now performed world-wide annually, the socioeconomic implication of this 30–40% restenosis rate has become a matter of serious concern to interventional cardiologists.

Restenosis is often the result of the balloon-mediated stretch and crush injury to the arterial wall and the possibility that the guide wires of the catheters used in such procedures during deployment cause injuries and can lead to proliferation of the smooth muscle cells of the artery, resulting in reclosure of the artery ("restenosis") over the following months.

Because of the potential complications, related to restenosis and the fear of dislodging an embolus from an ulcerative plaque and the severe resulting consequences, the application of repetitive angioplasty in the carotid arteries are severely limiting the options for minimally invasive intervention.

Attempts heretofore have been made to treat occlusions in the carotid arteries leading to the brain by a other types of interventions.

Carotid Endarterectomy is a surgical method for removal of blockages from the carotid arteries and is one of the most common vascular surgical procedures performed in the United States. Results from multicenter trials have demonstrated the efficacy of this procedure in the treatment of extracranial carotid disease in both symptomatic and asymptomatic patients (JAMA 1995; 273:1421–28; N Engl. J. Med. 1991; 325:445–53) and Endarterectomy procedures are used in the treatment of occlusive vascular disease in other vascular beds (Vasc. Surg. 1999;33:461–70).

In endarterectomy, the carotid artery is slit and plaque is removed from the vessel in the slit area. In a surgery, the carotid bifurcation is exposed through an incision in the neck of the patient and clamps are placed on either side of the occlusion to isolate it, and an incision made to open the artery. The occlusion is removed, the isolated area irrigated and aspirated, and the artery sutured closed. The clamps are removed to reestablish blood flow through the artery. The emboli and debris contained within the clamps may cause considerable problems after the carotid artery is opened, allowing blood to flow into the previously isolated area.

While endarterectomy is an effective therapy, it often leaves the adventitia and a significant area of thrombogenic subendothelium exposed. Despite the efficacy of carotid endarterectomy, the operation can lead to complications including thrombosis and the development of intimal hyperplasia causing complications that undo the beneficial effect of the intervention, or create new problems.

Clinical studies have demonstrated a post carotid endarterectomy stroke rate of 1–10% in the immediate postoperative period, almost all of which is accounted for by thrombus formation at the endarterectomy site with subsequent cerebral embolization (Stroke 1984; 15:950–55). Platelet accumulation may also result in restenosis due to intimal hyperplasia development, which may occur within two years postoperatively. Restenosis has been reported to occur in 10–20% of all endarterectomized patients at 2–5 years postoperatively, most of which is due to intimal hyperplasia, intimal thickening, and vessel diameter reduction as documented by carotid duplex ultrasonic scanning (J. Vasc. Surg. 1986; 3:10–23).

The cellular and molecular response of the vessel wall to mechanically induced trauma, surgical intervention, stent placement, placement of a vascular graft (arterial, or arteriovenous graft e.g., dialysis graft) is a complex interaction of inflammation, smooth muscle cell migration, proliferation and myofibroblast transformation that occurs as soon as the trauma occurs (Futura; 1997.p. 289–317). If the artery is severely damaged by disease, and perhaps hardened by calcium deposition, intervention may also cause some degree of additional injury with local de-endothelialisation and exposure of underlying extracellular matrix components such as collagen and elastin. In some patients the excessive recruitment of platelets and fibrinogen can then result in an acute thrombotic occlusion.

Studies using endarterectomized rat carotid artery models (Neurosurg 1985; 16:773–79), as well as embolectomy balloon injury models (Lab. Invest 1983; 49:327–33) have shown that as the endothelial cells are striped away during vascular injury, platelets begin to adhere to the exposed subendothelium. Spallone et. al. (Neurosurg 1985; 16:773–79) using scanning electron microscopy have shown that five minutes after a carotid endarterectomy in a rat, a monolayer of platelets is formed over the injured area. Fifteen minutes after the injury, platelet aggregation and thrombus formation are observed. Thirty minutes post endarterectomy, the site is covered with activated platelets and coated by fibrin and red blood cells. Thrombus formation reaches its peak at three hours post injury with a thick fibrin-platelet layer being observed. Platelets are an integral component of this thrombus formation and hence thrombosis, but they also appear to play a role in the development of intimal hyperplasia.

Studies using thrombocytopenic rats have further demonstrated a significant decrease in intimal thickening following carotid artery injury as compared to control rats (Proc. Natl. Acad. SCI USA 1989; 86:8412–16). Once platelets adhere to the exposed subendothelium of an injured vessel, they become activated and release their granules. These granules contain vasoactive and thrombotic factors (serotonin, ADP, fibrinogen, Von Willebrands factor, thromboxane A2), as well as growth factors (platelet derived growth factor, transforming growth factor-beta, and epidermal growth factor) (Circulation 1985; 72:735–40). The exact mechanisms by which platelets enhance the development of intimal hyperplasia are not yet completely understood. Studies suggest that platelets provide primarily a chemotactic stimulus for medial smooth muscle cell migration toward the intima during the second phase of intimal hyperplasia development (Vasc. Surg. 1991; 13:885–91). Other studies, using anti-PDGF antibodies, have demonstrated the vital role that PDGF plays in neointimal smooth muscle cell accumulation following a vascular injury (Science 1991; 253:1129–32). Another mechanism by which platelets may enhance the development of intimal hyperplasia is via the activation of the coagulation cascade and the subsequent accumulation of thrombin at the site of injury. Several studies have demonstrated the mitogenic effects of thrombin on smooth muscle cells (J. Clin. Invest. 1993; 91:94–98, J. Vasc. Surg. 1990; 11:307–13). In addition, thrombin has been shown to be a stimulus for platelet activation. Irrespective of the precise mechanism, platelet adhesion and activation at the site of a vascular injury play a significant role in the development of thrombosis and intimal hyperplasia and hence inhibition of platelet adhesion and activation may help prevent or reduce thrombosis rates and intimal hyperplasia development.

The adherence of platelets to the injured arterial wall is mediated in the first instance by von Willebrand factor (vWF), a multimeric glycoprotein that is released from endothelial cells and circulates in the plasma, where it functions as a carrier protein for factor VIII (Annu. Tev. Biochem. 1998; 67:395–424). Highly multimerized vWF also circulates contained within alpha-granules of platelets, from where it is released following platelet activation (Annu. Tev. Biochem. 1998; 67:395–424). Under elevated shear conditions, such as those encountered in arteries at sites of atheromatous plaque or mechanical intervention, vWF may bind, via its A3 domain, to surface-exposed collagen fibers (Biochemistry 1986; 25(26):8357–8361, Blood 1987; 70(5):1577–1583, J. Biol. Chem. 1987; 262(28):13835–13841). Collagen-bound vWF in turn then "tethers" platelets via shear-dependent exposure of an epitope in the vWF-A1 domain, which interacts with platelet GPIb/IX/V (Blood 1985; 65(1):85–90, Blood 1985; 65(4): 823–831, Br. J. Haematol 1986; 63(4):681–691). Thus vWF acts as a bridge between collagen and platelets and is a prerequisite for the adhesion of platelets to collagen under flow (J. Lab. Clin. Med. 1974; 83(2):296–300). Platelet rolling over vWF results in weak adhesion, however, and additional, direct interactions between collagen and other receptors on the platelet surface are required in order to facilitate permanent platelet adhesion, activation and aggregation (Thromb. Haemost 1997; 78(1):434–438, Thromb. Haemost 1997; 78(1):439–444). Direct collagen receptors on platelets include GP VI (Blood 1987; 69(6):1712–1720, Thromb. Haemost 1999; 81(5):782–792, J.Clin. Invest. 1989; 84(5):1440–1445), GP Ia/IIa ($\alpha_2/\beta_1$) (J.Clin. Invest. 1989; 84(5):1440–1445, Nature 1985; 318(6045):470–472), and to a lesser extent GP IV (CD36) (J. Biol. Chem. 1989; 264(13):7576–7583) and perhaps even p65 (J. Clin. Invest. 1997; 100(3):514–521). In the absence of vWF-assisted platelet binding, these receptors have proven to be too weak in mediating platelet recruitment to collagen in flow (Br. J. Haematol 1986; 63(4):681–691). Finally vWF, in combination with fibrinogen, facilitates the cross-linking and further activation of platelets via binding to platelet GP IIb/IIIa (J. Clin. Invest. 2000; 105(6):783–791), providing stability and strength to the developing thrombus.

With the advent of platelet GP IIb/IIIa and ADP receptor antagonists great strides forward in anti-aggregatory therapy have been made in recent years (Coronary Art Dis 1999; 10(8):553–560, J. Am. Coll. Surg. 2000; 191(1):76–92). However, these strategies are not designed to inhibit the initial adhesion of platelets to exposed collagen fibers, and despite the efficacy of GP IIb/IIIa antagonists in attenuating platelet-platelet interactions, platelets still adhere to the injured vessel wall (Blood 1993; 81(5):1263–1276, Circulation 1995; 91(5):1354–1362). Furthermore, platelet activation almost certainly extends beyond aggregation and acute thrombosis, the progression of sub-acute and chronic intimal hyperplasia being at least partially affected by mitogenic mediators such as platelet-derived growth factor (PDGF), released by the activation of platelets. Indeed, the inhibition of PDGF has been demonstrated to reduce intimal hyperplasia in various animal species (Science 1991; 253 (5024):1129–1132, Circulation 1999; 99(25):3292–3299).

The pathophysiological importance of vWF is suggested by the increase in circulating vWF in patients with acute myocardial infarction (Thromb Haemost 2000; 84:204–209, Circulation 1998; 98(4):294–299), with vWF levels being positively correlated with poor subsequent prognosis (Circulation 1998; 98(4):294–299). In vivo studies have further shown that neutralizing anti-vWF antibodies inhibit experimental thrombosis, confirming the essential role of vWF in thrombus formation (Thromb. Haemost 1998; 79(1): 202–210). Furthermore, with the ever more widespread use of angioplasty techniques in acute coronary syndromes, which invariably results in damage to the vessel wall and exposure of collagen, there is an increasing need for strategies that intervene pharmacologically as early as possible during the platelet adhesion-activation-aggregation cascade.

The two main lines of therapy, which are currently being used in an attempt to control platelet adhesion, activation and subsequent thrombosis and intimal hyperplasia, are anti-platelet agents and anti-thrombotic administration. Although drugs such as aspirin effectively block the synthesis of Thromboxane A2 through inhibition of the cyclooxygenase pathway, they do not prevent the collagen-induced platelet adhesion and activation, which stimulate the development of intimal hyperplasia. The use of heparin as an antithrombotic agent is associated with complications and limitations including a non predictable dose response, need for close laboratory monitoring, limited activity against clot bound thrombin, multiple inhibitory sites, antithrombin III dependency, a risk of major bleeding, as well as a need for continuous infusion. Clearly, an ideal therapeutic agent would be one that produces site specific and localized effects without systemic distribution or a generalized coagulopathy.

It appears that the vital steps which precipitate the cascade of events leading to thrombosis and later intimal hyperplasia stem from the interaction between the exposed subendothelial collagen at the site of vessel injury and a monolayer of platelets which adhere to the exposed collagen. Hence a specific inhibitor of the platelet to subendothelial collagen adhesion may serve to prevent or at least decrease the development of thrombus and intimal hyperplasia.

Several leech-derived substances have been reported to inhibit collagen-platelet interactions (Blood 1995; 85(3):705–711, Platelets 2000; 11(2):83–86, J. Biol. Chem. 1992; 267(10):6893–6898, J. Biol. Chem. 1992; 267(10):6899–6904, Blood Coagul Fibrinolysis 1991, 2(1):179–184). Destabilase, an isopeptidase with fibrin depolymerising activity isolated from *Hirudo medicinalis*, has been reported to inhibit platelet aggregation induced by various agonists, including collagen, but is believed to bind directly to the platelet membrane (Platelets 2000; 11(2):83–86). Leech antiplatelet protein (LAPP), a ~13 kDa protein from the saliva of *Haementeria officinalis*, inhibits platelet adhesion to collagen under static conditions (J. Biol. Chem. 1992; 267(10):6899–6904, Thromb. Haemost 1999, 82(3):1160–1163) and elevated flow (Arterioscler Thromb. Vasc. Biol. 1995, 15(9):1424–1431), with effects on both vWF- and platelet GP Ia/IIa-mediated binding to collagen (Thromb. Haemost 1999, 82(3):1160–1163). Calin is a ~65 kDa protein from *Hirudo medicinalis* for which a similar profile has emerged. Calin also inhibits collagen-platelet interactions under both static and flow conditions (Blood 1995; 85(3):705–711, Blood Coagul Fibrinolysis 1991, 2(1):179–184, Thromb. Haemost 1999, 82(3):1160–1163). Furthermore, both LAPP and Calin are potent inhibitors of collagen-induced platelet aggregation, inhibiting aggregation at concentrations similar to those which block vWF binding to collagen (J. Biol. Chem. 1992; 267(10):6893–6898, Blood Coagul Fibrinolysis 1991, 2(1):179–184, Blood 1995, 85(3):712–719).

Both LAPP and Calin have been evaluated in models of thrombosis in vivo, with mixed success. LAPP failed to reduce thrombus formation on collagen-coated grafts in a baboon arterio-venous shunt, despite the use of doses that inhibited collagen-induced platelet aggregation (Arterioscler Thromb 1993, 13(11):1593–1601), whereas Calin dose-dependently inhibited thrombus formation in a hamster model of venous thrombosis (Blood 1995, 85(3):712–719).

Non thrombogenic and anti thrombogenic coatings for stents and catheters are known in the art. The non thrombogenic coatings and products are based on modified and advanced polymers and examples are given in WO9301221 and WO9830615.

Anti thrombotic and anti restenosis coatings are in general biocompatible coatings that may also serve as reservoirs for local drug delivery. The coatings are mainly based on hydrogels and examples in the patent literature of methods for preparing various types of hydrogels and coating medical devices include WO9211896, WO9811828, WO0147572, EP0887369 and WO0139811.

The release profile of the therapeutic substances that are contained within the coating can be adjusted for example by varying the thickness of polymer layers or by selecting specific polymeric coatings that contribute selected physicochemical properties (such as charge, hydrophobicity, hydrophilicity) and or by preparing the coating as different layers. The criteria for selection of the polymer and the optimisation of release rate are understood by one of ordinary skill in the art. Other coatings are described by Fischell Circulation, 1996, 94:1494–95), Topol et al (Circulation, 1998, 98:1802–20) and McNair et al in device Technology, 1996, 16–22.

The use of stents, wires and catheters in the cardiovascular system is common practice and vessel wall injury, embolization and the following restenosis are a major concern of cardiologists during and after surgical intervention or catheterizations. Alternative methods such as endarterectomy cause comparable problems. Every procedure in which arteries are manipulated i.e. vascular surgery and angioplasty, is susceptible to the development of intimal hyperplasia. The utility of a method for preventing or decreasing the development of intimal hyperplasia can not be over emphasized, and the benefits of a method capable of doing this without producing systemic effects is even more encouraging.

Therefore the need for new and improved pharmaceuticals and methods for inhibiting the earliest events in pathophysiology (e.g. platelet adhesion) is obvious and contributions in this field are expected to substantially decrease morbidity and mortality associated with angioplasitic or surgical procedures.

DESCRIPTION OF THE INVENTION

In general, the present invention involves the introduction of the recently described platelet adhesion inhibitor Saratin into or onto a selected location within or on a lumen in a tissue, i.e. the vasculature or an organ under conditions such that Saratin may be used locally as a topical agent or as an adherent coating on the surface to prevent and inhibit an undesirable thrombotic and/or restenotic response to vessel wall injury, including injury associated with angioplasty, stents, dialysis graftsand other vascular grafts, and the treatment of benign hypertrophic scar formation as well as the treatment and passivation of unstable atherosclerotic plaques.

Saratin is a recently described (WO0056885) recombinant 12 kD, protein originally isolated from a leech. The protein inhibits vWF-dependent binding of platelets to arterial wall collagens under conditions of elevated shear and it is this aspect of the invention that makes Saratin suitable to inhibit arterial thrombosis. Another novel aspect is that Saratin can be used as a topical agent at the site of injury with the benefit of decreasing thrombosis and or intimal hyperplasia without any systemic effects. This represents a modality with specific and localized effects well suited for application by both surgeons and interventional radiologists alike.

Saratin can be combined with a variety of therapeutic agents for on-site delivery. Examples for use in coronary-artery applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), vasodilating agents, i.e., nitrates, calcium channel blocking drugs, anti-proliferative agents, i.e., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect pharmaceutical delivery focally within the vessel wall. By incorporation of the active agent in a swellable polymer, the active agent will be released upon swelling of the polymer.

In one embodiment the coating is made from a hydro-gel, such as poly-ethylene oxide, albumin, hydrophilic poly-methacrylates and hydrophilic poly urethanes.

The present invention further provides the use of Saratin and derivatives via local drug delivery devices/catheters or via stents and stent coatings and vascular grafts and graft coating technologies, for example. The invention also provides methods of administering Saratin in compositions that elute out regulated quantities of the Saratin over time in a localized area.

Figure 7A:
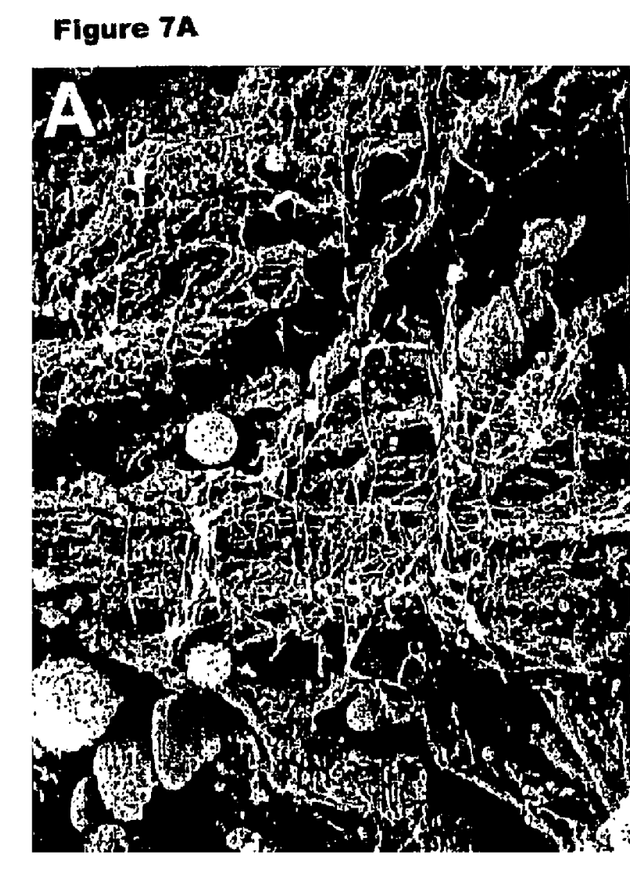
Figure 7B:
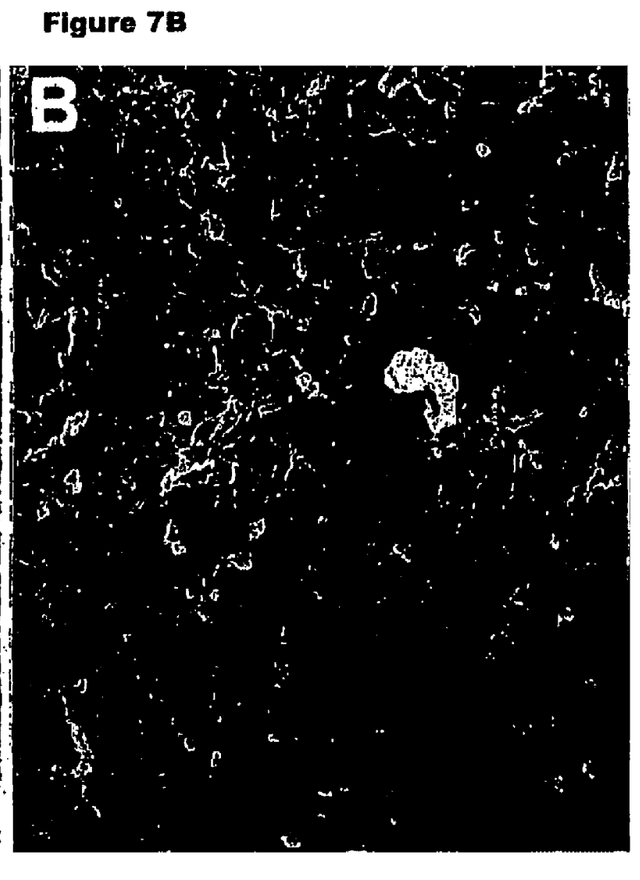

In particular, one embodiment of the present invention relates to uses of catheter-based devices to deliver Saratin locally. Saratin may as well be applied with or without other therapeutic agents out of a polymer matrix into body tissues using catheters. The basic requirements for the polymer material to be used in the present method are biocompatibility and drug release properties which can be adapted to the specifc application.

The local controlled Saratin release may be achieved by permeation only, iontophoresis only, electroporation only, or combined iontophoresis and electroporation may be used to release and incorporate Saratin efficiently inside the vessel lumen. Preferably, the catheter is able to perform procedures designed to maintain a high concentration of drug in the selected vessel space such that the results give an improved vessel coating with Saratin alone or with additional treatment agents.

The present invention is particularly applicable to the local delivery of Saratin during and after interventional cardiology procedures such as angioplasty and stent implantation and endarterectomy.

DETAILED DESCRIPTION OF THE INVENTION

Suitable recombinant Saratin for use in the invention was expressed and isolated from *Hansenula polymorpha* and was found to acts by blocking vWF binding to collagen and effectively prevents the adhesion of platelets to collagen under elevated shear. Saratin dose-dependently inhibited the binding of purified human vWF to human type I and III collagens ($IC_{50}$=0.23±0.004 and 0.81±0.04 $\mu$g $ml^{-1}$ respectively) and to calf skin collagen ($IC_{50}$=0.44±0.008 $\mu$g $ml^{-1}$). Furthermore, saratin showed a similar inhibitory potency against the binding of human, rodent and porcine plasma vWF to these collagens. In a flow chamber under conditions of elevated shear (2700 $s^{-1}$), saratin dose-dependently and potently inhibited platelet aggregate formation on a collagen-coated surface ($IC_{50}$=0.96±0.25 $\mu$g $ml^{-1}$), but at reduced shear (1300 $s^{-1}$) a rightward shift in the dose-response curve was noted ($IC_{50}$=5.2±1.4 $\mu$g $ml^{-1}$). Surface plasmon resonance analysis revealed both high and low affinity binding sites for saratin on human collagen type III ($K_d$=5×$10^{-8}$ M and 2×$10^{-6}$ M respectively), and although low concentrations of Saratin, that inhibited platelet adhesion under increased shear (i.e. saturation of high affinity binding sites) had no effect on vWF-independent collagen-induced platelet aggregation, high concentrations (i.e. saturation of low affinity binding sites) were found to inhibit platelet aggregation. These data demonstrate that saratin is a potent inhibitor of vWF-dependent platelet adhesion to collagen which forms the basis for the therapeutic potential as an anti-thrombotic agent.

The studies further demonstrated that Saratin potently and dose-dependently inhibits the binding of vWF not only to calf skin collagen, but to human collagen types I and III, both of which are abundant in arterial wall sub-endothelial layers and believed to be important in platelet-vessel wall interactions (Thromb Haemost 1997, 78(1):434–438). Since collagen-vWF-GP Ib/IX/V interactions only take place at sufficiently elevated shear, it was an important aspect of this invention to demonstrate the efficacy of saratin not only under static conditions, but also in an environment that more closely mimics the situation encountered in vivo. In a flow chamber, where shear forces can be varied to simulate such an environment, saratin clearly inhibited platelet accumulation to collagen, particularly at higher shear. The rightward shift of the dose-response curve as a result of reducing shear is noteworthy since the implication is that the efficacy of saratin in vivo may be localized to areas of high shear, where disruption of laminar blood flow results from changes to the endothelial surface presented to the blood, for example in the presence of atherosclerotic plaque or after mechanical intervention.

Surface plasmon resonance studies with saratin revealed that collagen may possess two independent binding sites for saratin, one of high affinity and one of low affinity. Inhibition by saratin of vWF binding to collagen is explained by saturation of the high affinity binding site, with $IC_{50}$ values around 5×$10^{-8}$ M, i.e. equal to the dissociation constant for this site. Because vWF-independent collagen-induced platelet aggregation was only inhibited at very high doses of saratin, (above 100 $\mu$M), it seems that saturation of the low affinity collagen binding site is associated with inhibition of direct collagen-collagen receptor interactions.

Another objective in this invention is the effect of Saratin to affect the local environment of an endarterectomized vessel without requiring systemic distribution and without altering platelet function or altering coagulation this makes it an ideal modality for topical application during vascular surgical and interventional radiological procedures.

In this spect of the invention the therapeutic Saratin effect was investigated using a rat carotid endarterectomy (CEA) model described previously (J. Vasc. Surg. 1998, 28:909–918). PLT activation is thought to be the initiating step in post CEA thrombosis and restenosis due to IH. It has been observed, that the topical application of Saratin on the lumenal surface will decrease the amount of platelet adhesion to the endarterectomized artery and thus decrease post-op thrombosis and IH.

As a summary of the exerimental results the anti platelet adherence effect of Saratin evaluated after two different postoperative times indicated that the number of adherent platelets at 3 hours (FIG. 4) and 24 hours (FIG. 5) post carotid endarterectomy was significantly reduced in the rats treated with Saratin as compared to the control rats.

Platelet adhesion was reduced by 59% at 3 hours (64±17.2 vs155±33.4 PLT per grid P=0.05) and 77% at 24 hours (35±11.3 vs 149±36.6 PLT per grid P=0110) Platelet adhesion was similar at 3 hours and 24 hours in the control groups but did show a decrease in the Saratin treated group from 64 to 35 platelets per grid.

FIGS. 6 and 7 show a typical representation of the endarterectomized surface with and without topical Saratin using scanning electron microscopy at 2000× magnification. FIG. 6A, shows the control surface at 3 hours post carotid endarterectomy, note the marked abundance of cellular material , fibrin strands, numerous red blood cells, and numerous platelets which are evident. FIG. 6B shows a Saratin treated surface 3 hours post carotid endarterectomy. Note the lack of cellular elements and the near barren collagen surface. FIG. 7A shows a control surface at 24 hours post carotid endarterectomy, platelets are evident as small white dots. FIG. 7B is a Saratin treated surface at 24 hours post carotid endarterectomy. There is a clear reduction in platelet adhesion with Saratin treatment.

Figure 6A:
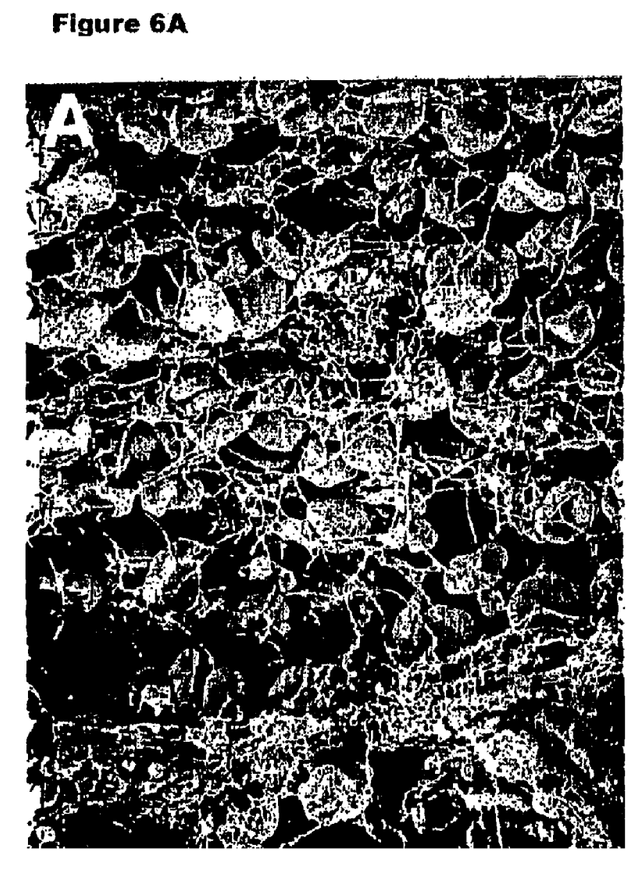
Figure 6B:
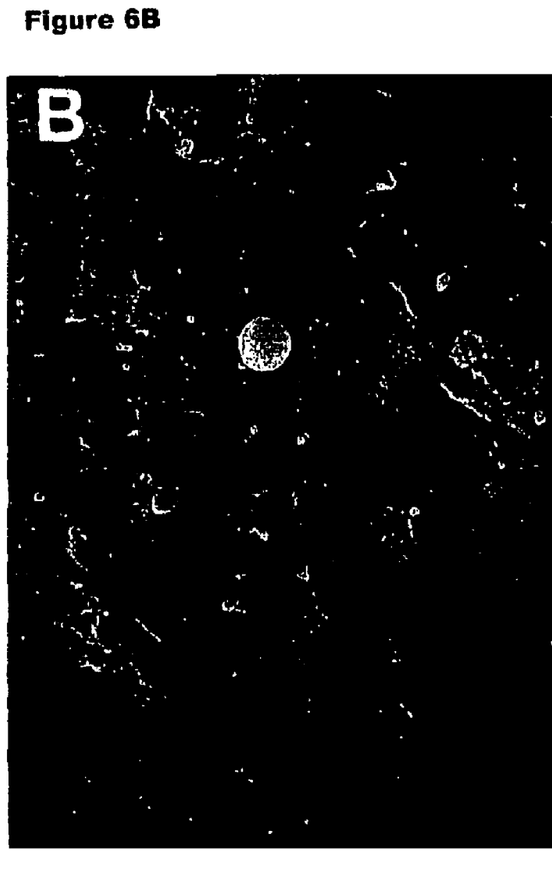

The application of topical Saratin following a carotid endarterectomy significantly decreased the development of intimal hyperplasia as compared to the control group. Percent lumenal stenosis as a measure of IH was significantly decreased with Saratin application compared to controls This decrease in IH formation correlated with the inhibition of PLT adherence. In terms of lumenal stenosis, control rats showed a 29.8±6.8%, p=0.0042 lumenal stenosis vs. a 10.9±1.8% lumenal stenosis in the Saratin treated group (FIG. 6). Saratin treated rats had 18.9% greater lumenal diameter than control rats. At two weeks post carotid endarterectomy, 5 of the 15 control rats (15%) developed complete thrombus of the carotid artery on histological analysis while 0 of 15 Saratin treated rats (0%) developed carotid thrombosis. A likelihood ratio Chi Square analysis revealed an odds ratio of 16.238 which suggests that the odds of the control group developing occlusive thrombosis was 16 times greater than the rats treated with Saratin P=0.0156.

No increased bleeding was encountered along the arterial suture line in the Saratin group. Bleeding times and systemic platelet counts were not found to change significantly in the Saratin treated rats as compared to control rats at 3 and 24 hours post endarterectomy.

The CEA model closely resembles the human CEA operation and hence the results propose a mechanism for decreasing the deleterious effects of platelet adherence and aggregation at the endarterectomy site without affecting platelet function systemically or decreasing hemostasis. The simple, topical application of Saratin during a rat CEA decreases platelet adherence, aggregation and subsequent restenosis in the carotid bed due to intimal hyperplasia.

Table 3 shows the results of the bleeding times and platelet counts. No statistically significant differences were observed between pre-op and post-op bleeding times. No statistically significant difference was identified in the platelet count differences between the Saratin and control rats.

Figure 4:
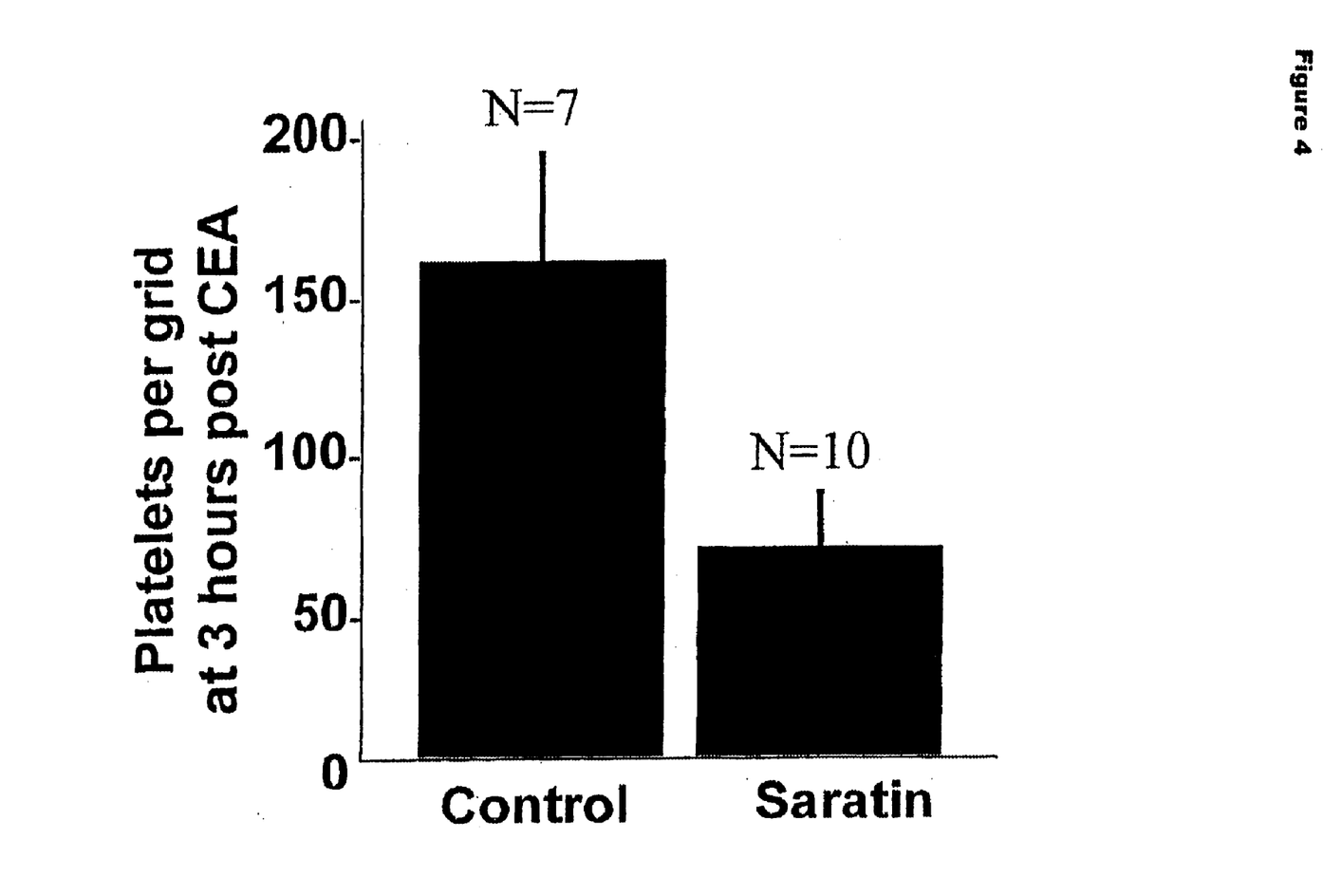
Figure 5:
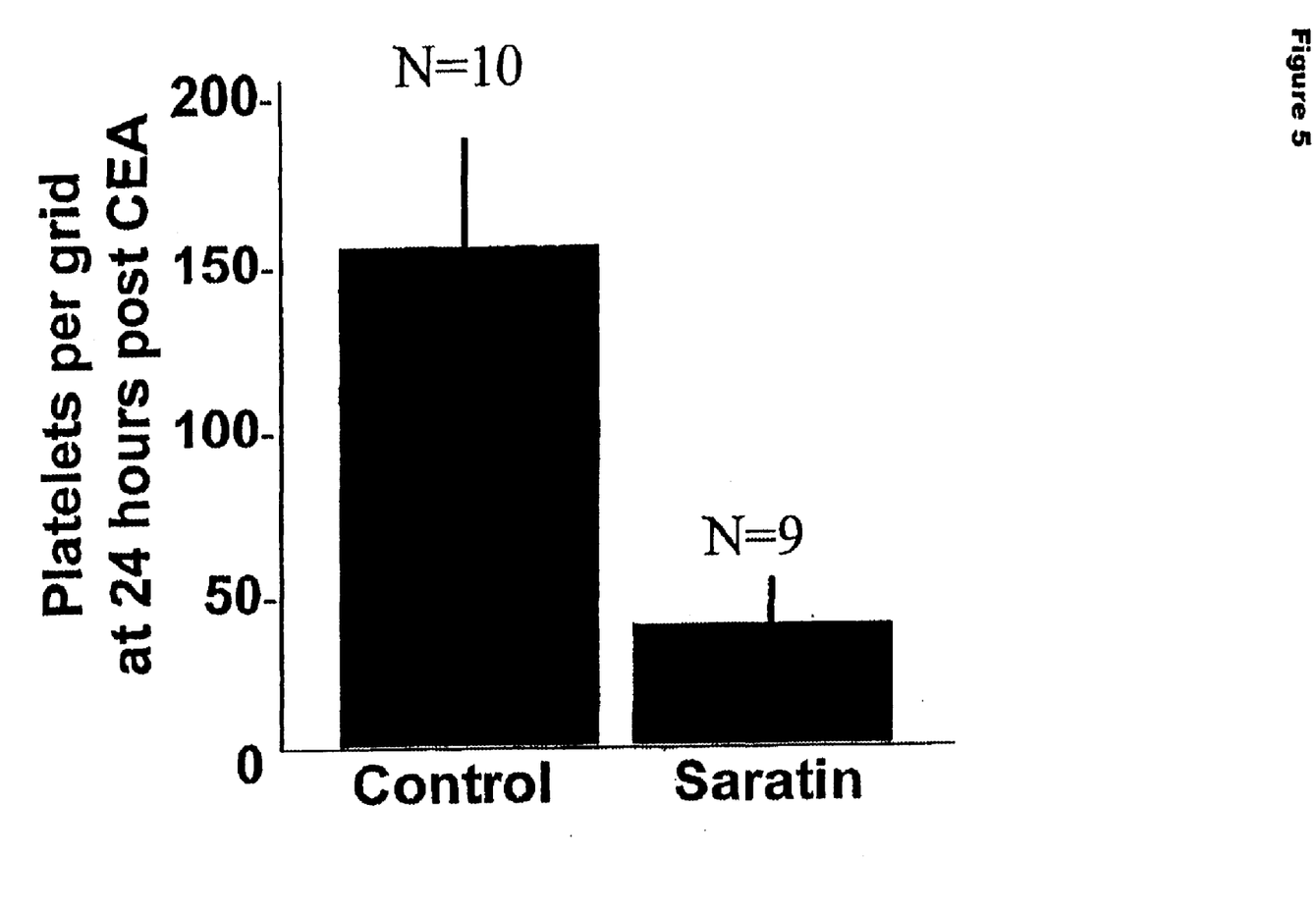
Figure 8:
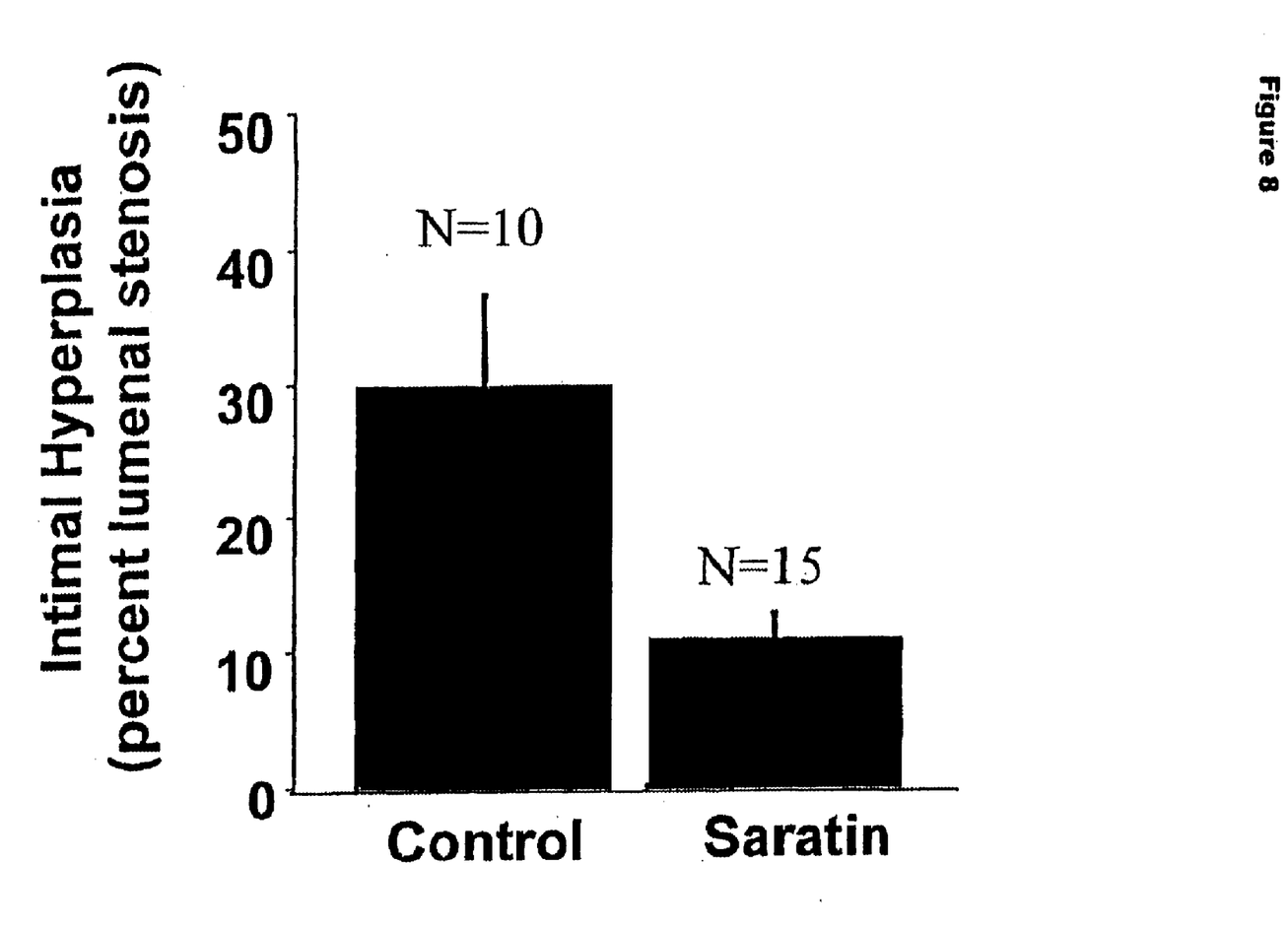
Figure 9A:
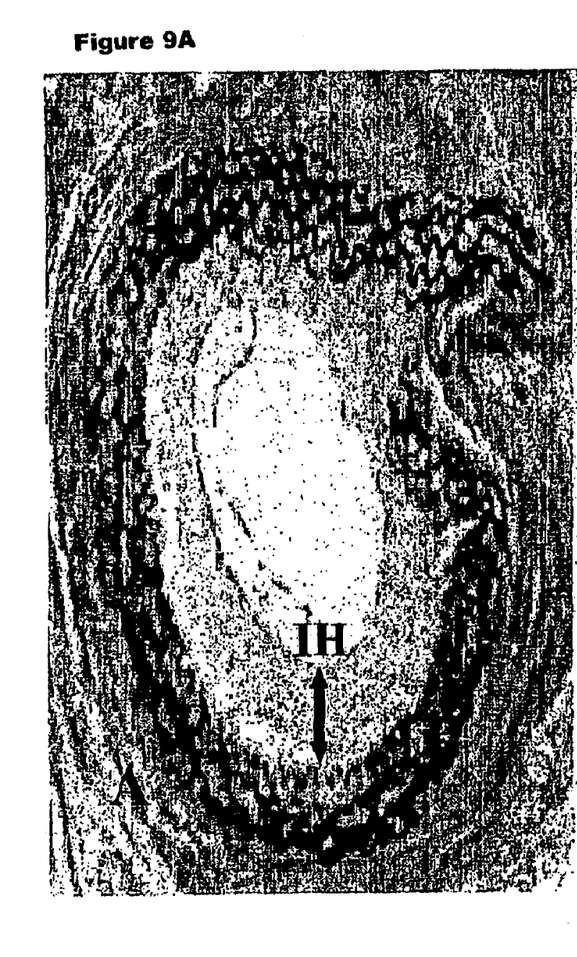
Figure 9B:
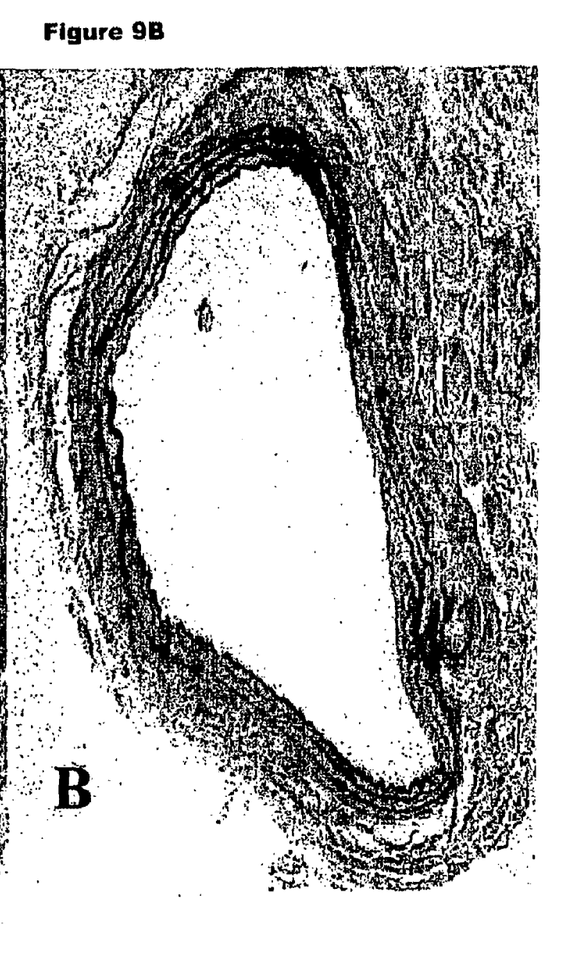

We have shown a significant decrease in platelet adhesion and accumulation after a vascular injury similar to endarterectomy. The decreased platelet adhesion is seen both immediately after endarterectomy (3 hours) as well as at 24 hours. The effect at 24 hours is significant in that we believe this effect is not due to the direct inhibitory effect of Saratin on the collagen (the serum half life of Saratin is 90 minutes), rather it is due to the initial inhibition of platelet aggregation and the subsequent disruption of the platelet activation cascade. Once platelets are initially inhibited from attaching to exposed collagen, the platelet cascade can not proceed. FIGS. 4 and 5 demonstrate that the topical application of Saratin on the recently injured vessel can inhibit platelet adhesion to a significant degree. Saratin inhibited platelet adhesion by 60% and 75% at 3 and 24 hours respectively. This inhibition is noted in the visible differences in cellular element deposition between control and Saratin treated arteries at both 3 hours and 24 hours (FIGS. 7 and 8). This lack of cellular response we propose is due to the inhibition of platelet adhesion. This represents a unique mode of therapy for the inhibition of platelet adhesion to an injured vessel. Control rats had a significantly reduced lumenal diameter at 2 weeks post carotid endarterectomy compared to Saratin treated rats (FIG. 9). The amount of intimal hyperplasia development was significantly reduced in Saratin treated rats, which correlated with reduced platelet adhesion and accumulation. The finding of decreased intimal hyperplasia and thrombosis that are associated with decreased platelet adhesion provide for clinically relevant endpoints and sequala of reduced platelet adhesion This demonstrated that the site specific non systemic inhibition of platelet aggregation and adhesion leads to a decreased thrombosis and occlusion rate and hence reduces the incidence of post carotid endarterectomy related cerebrovascular events. The level of intimal hyperplasia and lumenal stenosis improvement is further demonstrated by the significant finding of a decreased thrombosis rate in rats treated with Saratin. A full 33% of control rats showed thrombosis whereas none of the Saratin treated carotid arteries were thrombosed. Of particular clinical importance is the lack of systemic effects demonstrated by this agent. The local application of Saratin did not affect systemic bleeding times or platelet counts. This implies that the decreased platelet adhesion and the subsequent decrease in thrombosis and intimal hyperplasia are the result of local effects. These new findings related to Saratin are certainly important in that the spectrum of clinical applications for a modality that is capable of locally inhibiting the deleterious effects of platelet adhesion and activation without disturbing the systemic hemostatic mechanism, are many.

It has been pointed out earlier that various therapeutic interventions induce local injuries which would ideally be treated immediately and locally. Left untreated the injured cells initiate a series of processes involved in clotting, complement activation, and cellular response to release of cytokines, induction of proliferation, and other biologically active processes. It is difficult to stop these complex, interrelated processes once they have begun.

In the present invention it is therefore an important aspect that Saratin is located directly in the manipulated tissues. Another aspect of the local application is the minimization of potential problems related to the systemic effects of the drugs used for intervention.

Idealy Saratin treatment may be administered simultaneously with the appropriate therapeutic intervention which may be achieved by incorporating Saratin into the coating of a surgical device such as a balloon catheter or another device or part thereof. Another aspect could also involve the direct coating of the injured vessels with Saratin.

Additionally, normal Saratin delivery means may be used in the invention as well, such as free fluid form, including combinations with other therapeutic agents. However, use of polymer/hydrogel matrices has certain advantages over free fluid delivery. Delivery of an agent which has been incorporated into a polymer matrix does not require additional lumens in the support catheter to convey the free fluid drug solution into and out of the treatment site.

Additionally, the polymer matrices eliminate the risk of downstream leakage of drug solution due to defective balloon sealing of vessel segments, thereby avoiding the risk of exposure of non-target tissue to high concentrations of the drug.

A general technical solution to the local application of Saratin either on a medical device or as a coating to the injured vessel is for example the incorporation of Saratin into a polymer or hydrogel coating.

With respect to the polymer composition, the term "hydrogel" as used herein includes synthetic polymers with pores or interstices of different sizes and capacities and varying physicochemical properties especially with respect to the charge or the hydrophilic/hydrophobic nature of the gel matrix which may be introduced during manufacture of 
the coating or coated device. A variety of synthetic elastomers and naturally occurring polymeric materials are known to those skilled in the art. Saratin can be incorporated in the matrix either during polymer production or added after coating or molding of the polymer into the desired shape. Additionally, many of a number of different polymeric materials and methods of fabrication may be used to form the polymer matrices used in the present invention. Examples of suitable polymer materials or combinations include, but are not limited to, biocompatible and/or biodegradable polymers.

Several alkyl alkyl- and cyanoacrylates have been investigated for surgical use and some isobutyl cyanoacrylates have been found especially suitable.

A typical hydrogel polymer may be produced from a monomer mixture comprising 40–60 parts by weight of a purified monoester of a hydroxyalkyl alkyl acrylate having a single olefinic double bond, 40–60 parts by weight of a methacrylic monomer containing one olefinic double bond, and 0.001–5 parts by weight of a polymerization initiator. Polymerization may be accomplished by the conventional techniques of bulk polymerization, solution polymerization, suspension polymerization or emulsion polymerization. The polymerization technique used is dependent upon the volume of polymer required and the nature of the final product being produced. A typical hydrogel product would be described by a molar ratio of monoester to methacrylic monomer within the range of 1:1 to 2.3:1, preferably 1.5:1, wherein the pore diameter of the polymer is greater than 90 Angstroms.

As the monoester of a hydroxyalkyl acrylate having a single olefinic double bond, acceptable compounds include, but are not limited to, 2-hydroxyethyl methacrylate, glyceryl methacrylate, 2-hydroxypropyl methacrylate, glycidyl methacrylate, 2-hydroxyethyl acrylate, and 2-hydroxypropyl acrylate. Acceptable methacrylic monomers are methacrylic acid, methacrylamide 5 and methacrylonitrile.

The polymerization initiator may depend on the method of polymerization or the final intended use of the polymer. For example, where the polymer is to be formed as a solid object, free radical initiators may be used.

Preferred initiators of that type include difunctional polyesters such as 2,5-Dimethyl-2,5-bis(2ethylhexoylperoxy) hexane, or tertiarybutyl peroxypivilate. Alternatively, where the ultimate use of the polymer is as a coating applied in the form of the monomer mixture and polymerized in situ, the initiator may be radiation activated such as UV catalysts 2,2Azobis(2-methylpropionitrile) or azobisbutyronitrile (AIBN). The initiators are not restricted to use in a particular polymerization method or for a particular final product. For example, the free radical initiators may be employed in coatings and the radiation activated initiators may be employed in the formation of solid articles.

In addition to the substantially similar fractions of the monoester and methacrylic monomer, the monomer mixture may be enhanced with trace amounts of a longer chain alkyl acrylate or methacrylate ester comonomer such as cyclohexyl methacrylate, trimethylolpropane trimethacrylate or ethyleneglycol dimethacrylate. Such additional comonomers enhance the polymer crosslinking for situations where added polymer strength is desired. The trace amounts of these comonomers are generally less than 0.1% by weight of the total monomer mixture.

The hydrogel polymers used in the present invention may be formed to produce an article which is sufficiently crosslinked by intrinsic action that the resulting article requires no additional crosslinking monomers.

Additional examples for biodegradable polymers are poly (lactides), polyglycolides, polyanhydrides, polyorthoesters, polyactals, polydihydropyrans, polycyanoacrylates and copolymers of these and polyethylene glycol. These can take the form of co-polymer hydrogels or cross-linked polymer networks into which drugs for enhanced local delivery can be incorporated either during polymerization or, in the case of certain hydrogels, loaded subsequently. Preferable matrices would be tailored according to the molecular characteristics of the agent to control free diffusion outwards.

Multiple types of catheters and other medical devices coated with Saratin may be constructed and used according to the individual therapeutic need they have been designed for, or for the more specific purpose of delivering the Saratin loaded polymer locally: The present invention has been tested with the ballon catheter sold under the name Blue medical Devices BV GO available from Blue medical but is not limited to this type of catheter.

FURTHER EXAMPLES

Example 1

Purified vWF and Platelet Binding to Collagen Under Static Conditions vWF binding to collagen was investigated in microtiter plates, essentially as described elsewhere (Blood 1995, 85(3); 705–711). Various collagens, either human collagen type I, type III, or calf skin collagen (Sigma) were coated overnight by pipeting 50 $\mu$l of collagen, dissolved in 50 mM acetic acid at 125 $\mu$g ml$^{-1}$ in 96-well microtiter plates in the presence of 200 $\mu$l PBS, to promote renaturation. Following blocking non-coated sites with BSA, purified human vWF (1.25 $\mu$g ml$^{-1}$ for calf skin and collagen I coated plates; 0.625 $\mu$g ml$^{-1}$ for collagen III coated plates) or diluted normal plasma (human plasma: 1/80 on collagen I and III, 1/40 on calf skin collagen; hamster, mouse and porcine plasma: 1/80 on collagen III; 1/20 on collagen I and calf skin collagen) was added to the wells in the presence of Saratin and incubated for 2 hours (diluted plasma) or 1 hour (purified vWF). Binding of residual vWF to collagen was determined after a further washing step using rabbit anti-vWF antiserum (Dako, Copenhagen, Denmark) conjugated with horseradish peroxidase, which was developed and the resulting light absorbance measured at 492 nm.

When microtiter plates were pre-incubated with either human collagen I, human collagen III or calf skin collagen, the subsequent incubation of purified vWF in the presence of saratin was associated with a dose-dependent inhibition in vWF-collagen binding, with $IC_{50}$ values of 0.23±0.004, 0.81±0.04 and 0.44±0.008 $\mu$g ml$^{-1}$ respectively (FIG. 1). When purified vWF was replaced by diluted normal human plasma the inhibitory potency of saratin was maintained (Table 1). Saratin also inhibited the binding of vWF in diluted porcine, hamster and murine plasma to the different collagens tested, with consistently highest efficacy against collagen I (Table 1).

Example 2

Platelet Adhesion Under Elevated Shear

In view of the importance of shear forces in the control of vWF-dependent platelet adhesion to collagen (J. Lab. Clin. Med. 1974, 83(2):296–300), flow chamber perfusion studies were performed to examine the inhibitory action of saratin under similar flow conditions to those encountered in injured or diseased arteries. Calf skin collagen was coated on to plastic coverslips as previously described (Blood 1995, 85(3):705–711). Perfusions were performed in a parallel-plate perfusion chamber with two coverslip holders, and chamber heights of 0.4, 0.6 or 1.0 mm and a width of 1.0 cm, under pulsatile flow (roller pump, Watson Marlow 603S, VEL, Leuven, Belgium) at approximate shear rates of 2700, 1300 and 300 $s^{-1}$ respectively. Anticoagulated whole blood (0.2 IU $ml^{-1}$ low molecular weight heparin, Clexane) was perfused over the collagen-coated coverslips for 5 min, after which the rinsed coverslips were stained with Grünwald-Giemsa and assessed for platelet deposition by light microscopy and image analysis as described (Blood 1995, 85(3):705–711), using surface coverage as a quantitative parameter.

Figure 1:
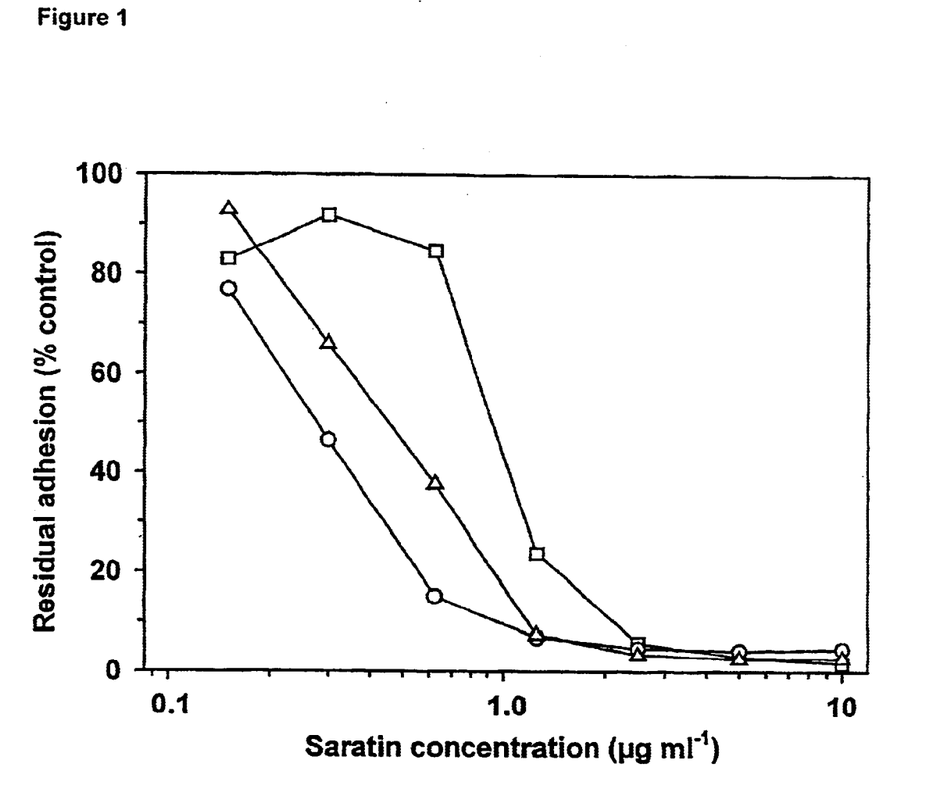
Figure 2:
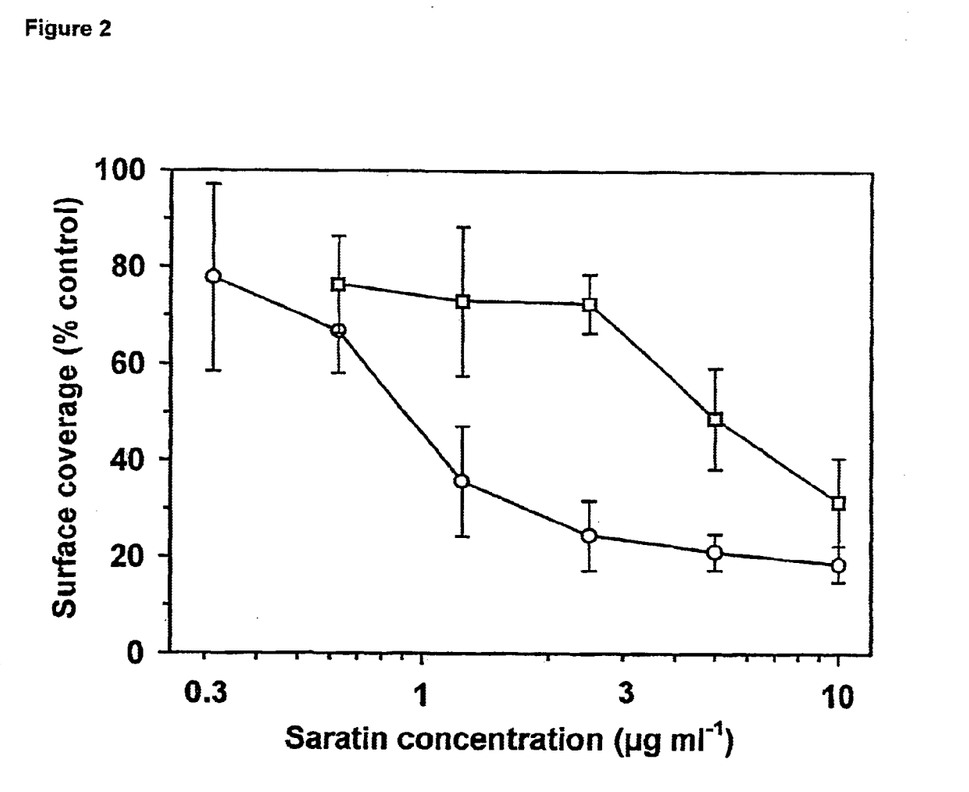

At a shear rate of 2700 $s^{-1}$, saratin dose-dependently inhibited platelet adhesion, with an $IC_{50}=0.96\pm0.25$ $\mu g$ $m^{-1}$, (FIG. 2). However, at a more moderate shear rate of 1300 $s^{-1}$, a distinct rightward shift in the dose-response curve was observed, with an $IC_{50}=5.2\pm1.4$ $\mu g$ $ml^{-1}$ (FIG. 2). At venous shear rates of 300 $s^{-1}$, saratin was unable to inhibit the adhesion of perfused platelets up to 10 $\mu g$ $ml^{-1}$ (data not shown).

Example 3
Binding Analysis by Surface Plasmon Resonance (SPR)

Protein interactions were identified and characterized by SPR using a BIAcore 3000 instrument (BIAcore, Freiburg, Germany). Coupling reagents were used according to protocols developed by the supplier. Coupling to the CM 5 sensor chip was done via activated carboxylate groups to free amine groups of human collagen type III (Sigma). The pH-scouting and the coupling chemistry was performed under standard conditions (Anal Biochem. 1991, 198(2): 268–277, JAI Press Ltd., 1992). For coupling the collagen was diluted to 0.125 $\mu g$ $ml^{-1}$ into 10 mM acetate buffer (pH 4.5), resulting in 331 resonance units (RU) immobilized material. This matrix was used to study the binding of purified recombinant saratin which was diluted into 20 mM Hepes (pH 7.4), 150 mM NaCl, 5 mM EDTA, 0.005% Tween 20. All binding experiments were performed at 25° C. Titrations with Saratin were performed at concentrations ranging from 7.8 nM to 10 $\mu M$. The resulting experimental RU plateau values were plotted according to the equation:

$$R_{eq}/\text{saratin concentration}=(-K_A \times R_{eq})+(K_A \times R_{max}).$$

Titration of saratin onto the immobilized collagen surface resulted in concentration-dependent binding. Further, the maximal amount of saratin bound to collagen on the sensor surface resulted in a signal greater than the calculated maximum signal for a 1:1 binding model. This points towards the existence of more than one binding site for saratin on collagen type III, further substantiated by the observation that fitting of the data to a 1:1 binding model according to Langmuir gave no satisfactory results.

Figure 3:
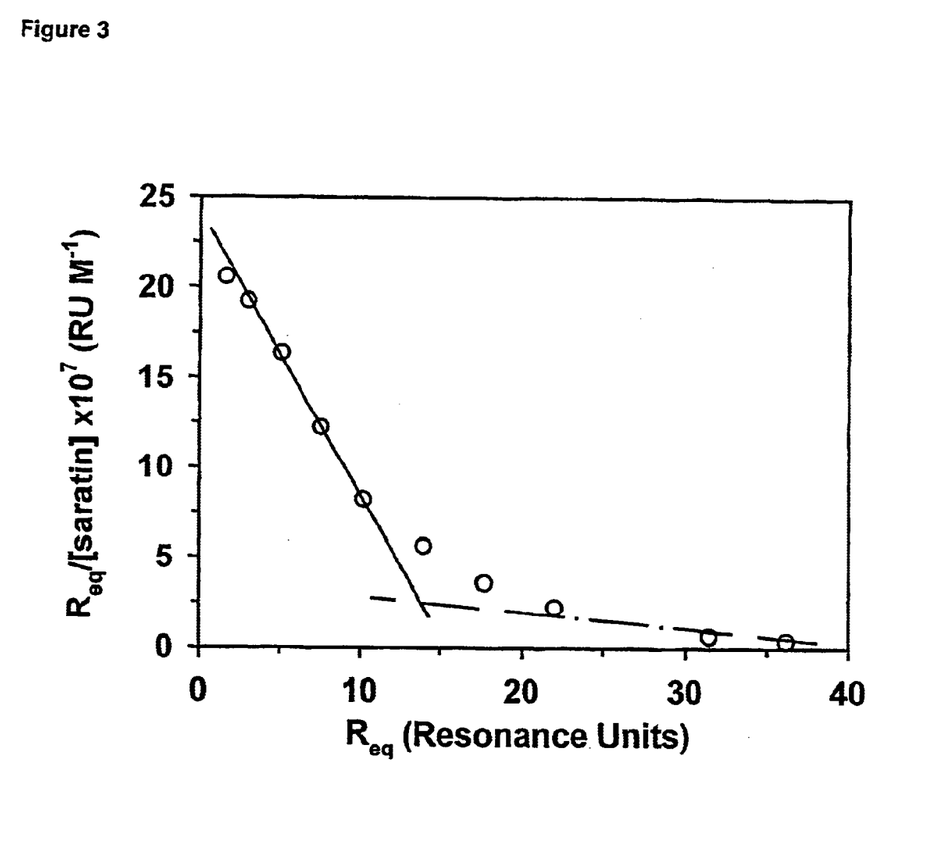

Scatchard analysis of the SPR data indicated the existence of two different binding sites with significantly different affinities for saratin (FIG. 3). Calculation of the equilibrium constants resulted in a dissociation constant of $5\times10^{-8}$ M for the high affinity site and $2\times10^{-6}$ M for the low affinity binding site.

Example 4
Platelet Aggregation

The specificity of saratin on platelet function was further evaluated via aggregation studies in platelet-rich plasma using collagen, ADP, ristocetin, arachidonic acid or the thromboxane mimetic U46619 as agonists. Citrated blood (3.13%) from unmedicated, healthy volunteers was centrifuged (15 min, 100 g) to obtain platelet-rich plasma, to which saratin was added (final concentration 0–200 $\mu g$ $ml^{-1}$) for 1 min prior to induction of platelet aggregation with collagen (0.5 $\mu g$ $ml^{-1}$), ADP (2.5 $\mu M$), ristocetin (0.9 mg $ml^{-1}$), arachidonic acid (1.0 mM) or U46619 (1.3 $\mu M$). The maximum aggregation (amplitude) over a 5 min period was observed for each agonist.

Saratin failed to inhibit maximal aggregation to all agonists tested, including collagen, at end concentrations up to 40 $\mu g$ $ml^{-1}$ (Table 2). Saratin was, however, able to partially inhibit collagen-induced platelet aggregation at 100 $\mu g$ $ml^{-1}$ (not shown), with complete inhibition at 200 $\mu g$ $ml^{-1}$, although aggregation to ADP was unaffected, even at 200 $\mu g$ $ml^{-1}$ saratin.

Example 5
Rat CEA Model

A rat CEA model that employed an open technique with arteriotomy, direct removal of intima and portions of media and suture closure of the artery was used. One group of rats received Saratin while the other group served as controls. Endpoint measurements included, 1) PLT adhesion, 2) Thrombosis rate, 3) Intimal hyperplasia development. Saratin was applied directly to the endaraterectomized surface of the carotid artery prior to arterial closure. Electron micrographs (2000×mag) of prepared carotid arteries were used for quantitative analysis of PLT aggregation. Total PLT numbers were counted using a standardized overlay grid. IH and thrombosis were assessed by computer assisted morphometric analysis of elastin stained carotid artery sections with direct measurement of IH area.

Example 6
Carotid Endarterectomy Operation

Animals were sedated with isoflurane in a bell jar, weighed, and then anesthetized with a combination of ketamine (100 mg/kg) and acepromazine maleate (1 mg/kg) intraperitoneally. After adequate anesthesia was confirmed with lack of response to hind paw stimulation, 4 cc of normal saline was injected subcutaneously in the region of the upper middle back to serve as a fluid bolus (10 cc/kg) to compensate for any intra-operative blood loss. The neck area was then shaved and preped with 7% isopropyl alcohol. Using sterile technique and a dissecting microscope (×40,sz40 Olympus, Olympus America Inc., Melville, N.Y.) a midline cervical incision was made. The superficial muscles were divided and the dissection carried down to the level of the right carotid artery. The cervical nerves in the region of the artery were dissected free to preserve pharyngeal function and prevent post-operative respiratory compromise.

After adequate carotid artery exposure, proximal and distal control at the bifurcation, approximately 1.5-cm apart, was obtained using 3-0 silk suture tourniquets. Using a corneal blade an arteriotomy was made and extended to 6 mm in length with micro-scissors. Using a 27-gauge needle, the intima was transversely scored across the vessel in two parallel lines, approximately 2 mm apart. The intima and medial layer were removed with micro-forceps. Saratin group rats received 5 $\mu l$ Saratin solution applied directly to the endarterectomized surface. The arteriotomy was closed with a running 10-0 monofilament nylon suture (MS/9, Ethilon, Ethicon Inc., Somerville, N.J.) beginning at the distal end. The distal tourniquet was removed first to assess for suture line hemostasis followed by removal of the proximal tourniquet. Time of Saratin application was 5 minutes, which represented the time of arteriotomy closure.

Any suture line bleeding was gently tamponaded with a sterile cotton tip applicator until hemostasis was achieved. The endarterectomized carotid artery was assessed with a hand held Doppler to confirm patency. The superficial muscle layer and skin were then closed with a running 3-0 absorbable suture.

Example 7

Platelet Adhesion

In the platelet adhesion subgroups, the rats were re anesthetized and the endarterectomized carotid arteries were harvested and fixed in a 4% glutaldehyde solution at 3 hours or 24 hours post carotid endarterectomy. During the harvesting procedure, the carotid segments were opened longitudinally along the site of the suture closure therefore exposing the endarterectomized area. The arteries were then postfixed with osmium tetroxide, dehydrated in a graded alcohol series, critical point dried with CO2 (1072 psi and 31.1° C.), coated with gold palladium, and placed in the scanning electron microscope (JEOL JSM 5410, JEOL, USA Peabody, Mass.). The endarterectomized areas were scanned at 2000× magnification and photographic images were obtained. The photographic images were matched and arranged in a collage allowing visualization of a greater area than was possible with a single field of the scanning electron microscope monitor. Once the collage of photographs was assembled, it was covered with a transparent overlay grid. The same overlay grid was used for all specimen photographs, 116 squares were used to count the total number of platelets in each photograph. The number 116 is the maximum number of squares that could be consistently counted on all of the photograph collages. Platelet counts were performed by two blinded observers.

Example 8

Intimal Hyperplasia

At two weeks post carotid endarterectomy, rats in the intimal hyperplasia group were anesthetized and the endarterectomized carotid artery exposed. The abdomen was opened in the midline and the distal aorta and inferior vena cava exposed. The vena cava was transected and the distal aorta cannulated with a 20-gauge catheter to infuse normal saline at 100 mm Hg until the vena cava effluent ran clear. Next, 10% buffered formalin was infused at 100 mm Hg in an equal volume to complete the perfusion-fixation technique. A one-centimeter section of the operated carotid artery was dissected free and placed in 10% formalin until further processing for histology. The arteries were paraffin blocked, sectioned, and elastin stained with Verhoeff's and Van Gieson's stain. Multiple sections were taken at intervals of 3 micrometers each continuing along the distance of the continuous 10-0 nylon suture arteriotomy closure to standardize the region of sectioning. The elastin-stained slides were photographed using a KODAK DC 120 Zoom digital camera (Eastman KODAK Company, Rochester, N.Y.). Any thrombosed sections were noted at this time. Non thrombosed images were downloaded into a computer and the lumenal areas of the carotids were analyzed using the National Institutes of Health (Bethesda, Md.),ImageJ Software program, Version 0.99i. This software package allowed us to delineate the inner area of the intimal hyperplasia and thus obtain an accurate measure of the cross-sectional area of the vessel lumen. Also, the outer area of intimal hyperplasia was determined. The difference between the two areas (outer area of intimal hyperplasia minus the actual lumen) was determined as the absolute area of intimal hyperplasia. Because the arterial cross section had individual variations of shape, the values were expressed as a ratio of the absolute area of intimal hyperplasia to the outer limit of intimal hyperplasia, and was reported as a percent lumen stenosis. This ratio represents the proportion of the lumen area occupied by intimal hyperplasia and allowed for comparison of the arterial cross sections of varying size(4). Minimal variability was seen between measurements with two blinded observers.

Example 9

Bleeding Times and Platelet Counts

In order to evaluate the effects of Saratin on systemic platelet counts and bleeding times, the platelet counts and bleeding times of 12 rats were determined. If it was necessary to obtain a preoperative blood sample from each rat of approximately 1–1.5 cc's, which represents a significant portion of a rats total blood volume. In view of this, it is reasonable to expect a decrease in the post operative platelet counts of both control and Saratin rats. In order to assess the effects of Saratin of platelet counts, we determined the difference in platelet counts for each rat by subtracting the preoperative platelet count from the postoperative platelet count to obtain a difference score. Differences in platelet counts were analyzed using a 2×2 factorial arrangement of treatments ANOVA model, which demonstrated no statistical significance in the platelet count differences between control and Saratin treated rats. All rats had their platelet counts and bleeding times determined preoperatively. Six rats underwent a carotid endarterectomy and were harvested 3 hours post op with bleeding times and platelet counts measured, and the remaining 6 rats were harvested 24 hours post op with bleeding times and platelet counts measured. Three of the rats in each time group received topical Saratin, and the remaining 3 rats served as controls.

Bleeding times were determined by transecting the distal 2 mm of the rat's tail and submerging approximately 4 cm's of the tail into a solution of phosphate buffered solution at 37° C. The amount of time elapsed from tail transection to cessation of bleeding was measured and was assigned as the bleeding time. Platelet counts were determined by drawing a 1–1.5 cc sample of blood from the internal jugular vein which was analyzed in a Coulter STKS blood analyzer and the results were expressed $\times 10^3$.

Example 10

Statistical Methods

Means±standard errors are reported. Unpaired t-test analysis were performed using the Stat View program (SAS Institute Inc. Cary, N.C. 27513) version 5.0 to compare Saratin treated and control groups for numbers of adherent platelets, percent lumenal stenosis and bleeding times. A likelihood ratio Chi Square analysis was used to evaluate the odds ratio for development of thrombosis two weeks post carotid endarterectomy. A 2×2 factorial arrangement of treatments ANOVA model was used to evaluate the differences between preoperative and postoperative platelet counts.

Example 11

Experimental Animals

Sprague-Dawley rats (350–400 g) were organized into carotid endarterectomy groups based on two main objects. 1) Evaluation of platelet adhesion and 2) Evaluation of lumen stenosis due to intimal hyperplasia, and thrombosis rate. Within these two objectives, rats were divided into control and Saratin treated animals. All rats underwent a carotid endarterectomy (see below), Saratin treated rats received a topical application of 5 µl solution of Saratin on the lumenal surface of the carotid artery immediately after 
removal of the intima/media layer. The platelet adhesion group consisted of electron microscopy evaluation at 3 hours post carotid endarterectomy (n=17) and 24 hours post carotid endarterectomy (n=19). The intimal hyperplasia group (n=25) were harvested two weeks post carotid endarterectomy.

Example 12
Preparation of Saratin Coated Hydrogel Catheter

Surfaces of PA-12 based materials have been activated by emersing the devices in a solution of 2 mol-% macro-initiator (poly(octadecen-alt-malein acetic acid anhydrid) with a per-ester (11–16 mol-%) dissolved in isopropanol and 0,5 mol ethylenglykol-dimethacrylat (EGDMA)/1 mol macro-initiator. After drying the macro-initiator-/EGDMA coating. The coating has been annealed another 5 bis 10 min at 120° C. which helped to improve fixation of the macro-initiator to the surface thus improving crosslinking.

For optimising coating conditions hydrogel coatings generated on a PA-12 carrier sheet have been used. Prior to coating, the sheets have been washed with isopropanol or aceton and dried.

Ballon catheter type Blue Medical Devises GO (RX PTCA catheter) consiting of Vestamid (PA-12) have been used for coating with hydrogel. Aqueous solutions of 5 mol-% acrylic acid 100 ml and 0,2 bis 0,8 mol-% methylen-bis-acrylic have been mixed and used to coat sheets or catheters. After polymerisation the coated device has been washed with water and for another 24 hrs in PBS buffer.

Following this, the polymer is annealed in the oven at 60–80° C. for 0,5 to 3 hours.

Thickness of dried hydrogel coatings was in a range of 1 to 4 $\mu$m, the swelling of hydrogel in aqueous solution ranged from 10 to 50 g hydrogel wet/1 g hydrogel dry.

When immersed (30 min) in a buffered PBS buffer pH 7,4 solution of Saratin a concentration of 50 $\mu$gml has been used.

Organic solvents have been used to prepare the coating solutions when sprayed on a ballon catheter using standard small scale spray coating equipment like that available from EFD.

FIGURE LEGENDS

FIG. 1. Effect of saratin on purified human vWF binding to human collagen types I (circles) & III (squares), and calf skin collagen (triangles). $IC_{50}$ with type I=0.23±0.004 μg $ml^{-1}$, type III=0.81±0.04 μg $ml^{-1}$ & calf skin collagen=0.44±0.008 μg $ml^{-1}$.

FIG. 2. Effect of shear on the inhibition by saratin of platelet aggregate formation on human collagen type III in a flow chamber in vitro. Circles indicate a shear rate of 2700 $s^{-1}$ ($IC_{50}$=0.96±0.25 μg $ml^{-1}$), whereas squares indicate a shear rate of 1300 $s^{-1}$ ($IC_{50}$=5.2±1.4 μg $ml^{-1}$).

FIG. 3. Scatchard analysis of saratin binding to immobilized human collagen as detected by surface plasmon resonance, indicating the presence of a high affinity ($K_d$=5×$10^{-8}$ M, solid line) and a low affinity ($K_d$=2×$10^{-6}$ M, broken line) binding site for saratin on collagen III.

FIG. 4. Number of platelets adherent to the exposed subendothelial surface 3 post carotid endarterectomy, comparing Saratin application (n=7) and control groups (n=10). Data are means±SE. The Saratin group received 5 μl of Saratin solution applied topically to the exposed subendothelial surface. Star indicates a P value of 0.05.

FIG. 5. Number of platelets adherent to the exposed subendothelial surface 24 hours post carotid endarterectomy comparing Saratin application (n=9) and control groups (n=10). Data are means±SE. Platelets were counted using the scanning electron microscope. The Saratin group received 5 μl of Saratin solution applied topically to the exposed subendothelial surface. Star indicates a P value of 0.01.

FIG. 6. Electron micrograph (2000×) of an endarterectomized rat carotid artery 3 hours post carotid endarterectomy. A, control surface. B, surface receiving topical Saratin (5 μl). The control surface shows abundant cellular elements including fibrin strands, red blood cells, and platelets. The Saratin treated surface shows a marked decrease in cellular elements.

FIG. 7. Electron micrograph (2000×) of an endarterectomized rat carotid artery 24 hours post carotid endarterectomy. A, control surface. B, surface receiving topical Saratin (5 μl). The control surface shows numerous red blood cells and platelets. The Saratin treated surface shows a marked decrease in platelet adhesion.

FIG. 8. Percent lumenal stenosis secondary to intimal hyperplasia 2 weeks post carotid endarterectomy. Saratin (n=15), and a control group (n=10) are shown. Saratin group received 5 μl of Saratin applied topically to the exposed subendothelial surface. Star indicates a P value of 0.004.

FIG. 9. Cross sections through carotid arteries showing reduction of intimal hyperplasia in Saratin treated arteries (B) as compared to the untreated control (A) in the rat. IH=intimal hyperplasia Table 1. $IC_{50}$ concentrations of saratin necessary to inhibit platelet adhesion in PRP from various species binding to human collagen types I & II, and calf skin collagen.

Table 2. Effect of saratin on the maximum platelet aggregation (%) in PRP induced by various agonists, with end concentrations of reagents as indicated.

Table 3. Preoperative and postoperative bleeding times and platelet counts.

TABLE 1

| | Saratin $IC_{50}$ (μg $ml^{-1}$) | | |
|---|---|---|---|
| Plasma source | Collagen type I | Collagen type III | Calf skin collagen |
| Human | 0.2 | 0.9 | 0.3 |
| Porcine | 0.2 | 0.5 | 0.5 |
| Hamster | 0.4 | n.t. | 7.0 |
| Murine | 0.1 | 0.6 | 0.3 |

TABLE 2

| | Aggregation (%) at indicated saratin concentration (μg $ml^{-1}$) | | | | |
|---|---|---|---|---|---|
| Agonist | 0 | 10 | 20 | 40 | 200 |
| Collagen (0.5 μg $ml^{-1}$) | 62 | 67 | 63 | 64 | 0 |
| ADP (2.5 μM) | 66 | 64 | 69 | 82 | 88 |
| Ristocetin (0.9 mg $ml^{-1}$) | 61 | 67 | 75 | 63 | n.t. |
| Arachidonic acid (1.0 mM) | 66 | 66 | 67 | 57 | n.t. |
| U46619 (1.0 μM) | 66 | 65 | 57 | 56 | n.t. |

TABLE 3

| TIME | CONDITION | PLATELET COUNT | BLEEDING TIME |
|---|---|---|---|
| PRE OP | CONTROL | 752 ± 36.05 × $10^3$ | 11.9 ± .91 min |
| PRE OP | SARATIN | 829 ± 33.85 × $10^3$ | 8.6 ± .62 min |

TABLE 3-continued

| TIME | CONDITION | PLATELET COUNT | BLEEDING TIME |
|---|---|---|---|
| 3 HOURS | CONTROL | $604 \pm 34.2 \times 10^3$ | $10.8 \pm .9$ min |
| 3 HOURS | SARATIN | $590 \pm 76 \times 10^3$ | $9.1 \pm .5$ min |
| 24 HOURS | CONTROL | $694 \pm 117 \times 10^3$ | $12.9 \pm 1.1$ min |
| 24 HOURS | SARATIN | $729 \pm 19 \times 10^3$ | $11.5 \pm 1.3$ min |

What is claimed is:

1. A method for treating vascular injury or endarterectomy comprising administering to the vascular tissue a therapeutically effective amount of Saratin, wherein the vascular injury is associated with atherosclerosis, restenosis, cardiac transplant vasculopathy, rotablation, dialysis graft shunts and other graft anastomoses, benign hypertrophy, or benign prostatic hypertrophy.

2. The method according to claim 1, wherein the Saratin is administered locally via a catheter or wherein Saratin is incorporated into endoluminal paving of a catheter which is directed locally to the tissue.

3. The method of claim 1, wherein Saratin is incorporated into a locally administered polymer that permits local sustained release of Saratin.

4. The method of claim 3, wherein the polymer formulated Saratin is administerd locally via a catheter.

5. A method according to claim 3, wherein the polymer is poly-ethylene oxide, albumin, hydrophilic polymethacrylate or hydrophilic poly urethane.

6. The method of claim 1, wherein Saratin is incorporated into a stent or stent coating which is placed locally on or in the tissue.

7. The method of claim 1, wherein Saratin is incorporated into an endovascular graft or an endovascular graft coating which is placed locally on or in the tissue.

8. The method according to claim 1, wherein the endarterectomy is carotid endarterectomy.

9. A method according to claim 1, wherein Saratin prevents platelet adhesion, thereby inhibiting thrombosis and restenosis.

10. A method according to claim 1, wherein Saratin inhibits platelet accumulation.

11. A method according to claim 1, wherein the Saratin administered with a prostacyclin, a thrombolytic agent, a streptokinase, an urokinase, a tissue plasminogen activator (TPA), an anisoylated plasminogen-streptokinase activator complex (APSAC), a vasodilating agent, a nitrate, a calcium channel blocking drug, an anti-proliferative agent, colchicines, an alkylating agent, an intercalating agent, a growth modulating factor, an interleukin, a transforming growth factor-beta, a monoclonal antibody directed against a growth factor, a steroidal anti-inflammatory agent, a non-steroidal anti-inflammatory agent, an agent that modulates arteriosclerosis, or an antibiotic.

12. A method of treating injured vascular tissue, comprising locally administering to the injured vascular tissue a therapeutically effective, amount of Saratin, thereby treating the injured vascular tissue wherein the vascular injury is associated with atherosclerosis, restenosis, cardiac transplant vasculopathy, rotablation, endarterectomy, dialysis graft shunts and other graft anastomoses, benign hypertrophy, or benign prostatic hypertrophy.

13. The method of claim 12, wherein Saratin is locally administered via a catheter.

14. The method of claim 12, wherein Saratin is incorporated into endoluminal paving of a catheter which is directed locally to the tissue.

15. The method of claim 12, wherein Saratin is incorporated into a locally administered polymer that permits local sustained release of Saratin.

16. The method of claim 12, wherein the polymer formulated Saratin is administerd locally via a catheter.

17. The method of claim 12, wherein Saratin is incorporated into a stent or stent coating which is placed locally on or in the tissue.

18. The method of claim 12, wherein Saratin is incorporated into an endovascular graft or an endovascular graft coating which is placed locally on or in the tissue.

19. A method according to claim 12, wherein Saratin inhibits platelet accumulation.

20. A method according to claim 12, wherein the local controlled Saratin release is achieved by permeation, iontophoresis, electroporation, or combined iontophoresis and electroporation.

21. A method according to claim 12, wherein Saratin is a 12 kD recombinant protein.

* * * * *